United States Patent
Hongo et al.

(10) Patent No.: US 9,359,397 B2
(45) Date of Patent: Jun. 7, 2016

(54) METHOD FOR MANUFACTURING PROTEIN DRUG

(75) Inventors: Tomoko Hongo, Tokyo (JP); Hirohisa Hayashida, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 14/127,291

(22) PCT Filed: Jun. 22, 2012

(86) PCT No.: PCT/JP2012/065987
§ 371 (c)(1),
(2), (4) Date: Mar. 28, 2014

(87) PCT Pub. No.: WO2012/176876
PCT Pub. Date: Dec. 27, 2012

(65) Prior Publication Data
US 2014/0199262 A1    Jul. 17, 2014

(30) Foreign Application Priority Data

Jun. 24, 2011  (JP) .................................. 2011-141121

(51) Int. Cl.
| C07K 1/34 | (2006.01) |
| C07K 16/00 | (2006.01) |
| B01D 61/14 | (2006.01) |
| C07K 16/06 | (2006.01) |
| A61K 38/00 | (2006.01) |

(52) U.S. Cl.
CPC . *C07K 1/34* (2013.01); *B01D 61/14* (2013.01); *C07K 16/00* (2013.01); *C07K 16/065* (2013.01); *A61K 38/00* (2013.01); *B01D 2311/14* (2013.01); *B01D 2311/18* (2013.01)

(58) Field of Classification Search
None
See application file for complete search history.

(56) References Cited

U.S. PATENT DOCUMENTS

| 4,808,315 A | 2/1989 | Manabe et al. |
| 4,857,196 A | 8/1989 | Manabe et al. |
| 6,365,395 B1 | 4/2002 | Antoniou |
| 7,919,592 B2 | 4/2011 | Lengsfeld et al. |
| 7,932,355 B2 * | 4/2011 | Chtourou et al. ............ 530/383 |
| 2003/0232969 A1 | 12/2003 | Lengsfeld et al. |
| 2006/0127874 A1 | 6/2006 | Sato et al. |
| 2012/0077963 A1 * | 3/2012 | Hongo et al. ............ 530/388.1 |

FOREIGN PATENT DOCUMENTS

| CN | 1705490 A | 12/2005 |
| EP | 0911037 | 4/1999 |
| EP | 2078730 | 7/2009 |
| EP | 2 412 817 | 2/2012 |
| JP | 1-148305 | 6/1989 |
| JP | 2001-335509 | 12/2001 |
| JP | 2003-012693 | 1/2003 |
| JP | 2003-274941 | 9/2003 |
| WO | 96/00237 | 1/1996 |
| WO | 2010/109920 | 9/2010 |
| WO | 2011/058284 | 5/2011 |

OTHER PUBLICATIONS

International Search Report for PCT/JP2012/065987, mailed Jul. 17, 2012.
Manabe, "Removal of Virus Through Novel Membrane Filtration Method," Dev. Biol. Stand., vol. 88, pp. 81-90, 1996.
Brandwein and Aranha-Creado, "Membrane Filtration for Virus Removal," Dev. Biol., vol. 102, pp. 157-163, 1999.
Aranha-Creado et al., "Clearance of Murine Leukaemia Virus from Monoclonal Antibody Solutions by a Hydrophilic PVDF Microporous Membrane Filter," Biologicals, vol. 26, pp. 167-172, 1998.
Moce-Llivina et al., "Comparison of Polyvinylidene Fluoride and Polyether Sulfone Membranes in Filtering Viral Suspensions," Journal of Virological Methods, vol. 109, pp. 99-101, 2003.
Liu et al., "Recovery and purification process development for monoclonal antibody production", *mABs*, vol. 2, No. 5, pp. 480-499, Sep. 1, 2010.
European Search Report for EP 12803267.9, mailed Mar. 20, 2015.

* cited by examiner

*Primary Examiner* — James H Alstrum Acevedo
*Assistant Examiner* — Tara Martinez
(74) *Attorney, Agent, or Firm* — Greenblum & Bernstein, P.L.C.

(57) ABSTRACT

The present invention provides a method for manufacturing a virus-free protein drug, comprising (a) a filtration step of filtering a virus-containing protein solution through a small-pore size virus removal membrane to obtain a virus-free protein solution, the filtration step (a) comprising (q) a low-pressure filtration step of filtering the solution through the small-pore size virus removal membrane at a filtration pressure of 0.30 kgf/cm$^2$ or lower to obtain the virus-free protein solution, wherein the solution prior to filtration in the low-pressure filtration step (q) has a pH (X) and a salt ionic strength (Y (mM)) that satisfy the following equations 1 and 5: $0 \le Y \le 150X - 590$ (Equation 1) and $3.5 \le X \le 8.0$ (Equation 5) or the following equations 4 and 5: $Y=0$ (Equation 4) and $3.5 \le X \le 8.0$ (Equation 5).

21 Claims, 1 Drawing Sheet

METHOD FOR MANUFACTURING PROTEIN DRUG

TECHNICAL FIELD

The present invention relates to a method for manufacturing a virus-free protein drug and a virus-free protein drug obtained by the manufacturing method.

BACKGROUND ART

Protein drugs typified by biomedicines, plasma derivatives, and the like have raised concerns about contamination by ingredient-derived or process-derived viruses. Thus, when such protein drugs are manufactured, the inactivation or removal of viruses in the drugs is very important from the viewpoint of the safety and stability of the drugs. This inactivation of viruses has been practiced by a method such as heat treatment or treatment with chemical agents. These treatments, however, are not sufficient in themselves for the inactivation of viruses. In addition, these methods might denature the proteins themselves in the drugs. Against this backdrop, the viruses are separated and removed by filtration using virus removal membranes as physical virus removal means without chemical denaturation (e.g., Patent Literatures 1 to 3).

Virus removal membranes made of natural materials such as cellulose or of synthetic polymer materials such as polyvinylidene fluoride (PVDF) or polyether sulfone (PES) are known (Non Patent Literatures 1 to 4). Particularly, in the case of protein solutions containing small protein molecules, small-pore size virus removal membranes having a pore size that does not permit permeation of viruses but permits permeation of the protein molecules are used.

Ideally, the filtration of virus-containing solutions using a virus removal apparatus equipped with a virus removal membrane should filter larger amounts of protein solutions in a short time and should exert sufficiently high virus removal performance. To treat larger amounts of protein solutions in a short time, filtration of virus-containing solutions is generally carried out at a pressure as high as possible. However, the continuation of such high-pressure filtration may leave inside the membrane, proteins supposed to be contained in filtrates. In addition, recent protein drugs tend to have higher concentrations of proteins. Along with this tendency, there is also a growing demand for higher protein concentrations in the filtration step for removing viruses. In the case of filtering high-concentration protein solutions through a small-pore size virus removal membrane, clogging frequently occurs, particularly, due to proteins remaining inside the membrane.

Such proteins remaining inside the small-pore size virus removal membrane are recovered by filtration with a protein-free buffer solution (usually, the same as a buffer solution used for dissolving the proteins) as a washing solution. This filtration step is added after the protein filtration and therefore called post-wash or post-filtration. For this post-wash, typically, the filtration pressure is temporarily relieved in order to have a switching, at an entrance of solution to be filtered, from a line for protein solutions to a line for washing solutions. If the filtration pressure is not decreased, the solution flows backward to the washing solution side.

Examples of such decrease in filtration pressure during filtration through a virus removal membrane, as in the post-wash step, include a case in which pressurization is suspended during filtration for a reason such as a power failure (this case is called stop and start).

Depending on the types of protein drugs, low filtration pressures may be desirable for filtration through a virus removal membrane during manufacturing of the drugs. Such filtration at low filtration pressures is often carried out in order to increase the final throughputs of solutions that tend to cause clogging or in order to increase the rate of permeation or recovery of solutions of high-molecular proteins in elongated shapes. When low filtration pressures are adopted, specific filtration pressures are often determined to balance permeability and productivity and also depend on the concentrations, etc. of the protein drugs to be obtained. For example, Patent Literature 4 has adopted a filtration pressure on the order of 0.15 $kgf/cm^2$.

CITATION LIST

Patent Literature

Patent Literature 1: Japanese Patent Laid-Open No. 2001-335509
Patent Literature 2: Japanese Patent Laid-Open No. 2003-274941
Patent Literature 3: International Publication No. WO 2010/109920
Patent Literature 4: U.S. Pat. No. 7,932,355

Non Patent Literature

Non Patent Literature 1: Manabe S, Dev. Biol. Stand., (1996) 88: 81-90
Non Patent Literature 2: Brandwein H et al., Dev. Biol. (Basel), (2000) 102: 157-63
Non Patent Literature 3: Aranha-Creado et al., Biologicals, (1998) June; 26 (2): 167-72
Non Patent Literature 4: L. Moce-Llivina et al., Journal of Virological Methods, (2003) April, Vol. 109, Issue 1, Pages 99-101

SUMMARY OF INVENTION

Technical Problem

In the conventional filtration of protein solutions using virus removal membranes, attentions have been focused on methods performed at a pressure as high as possible in order to increase throughputs and enhance efficiency. Sufficient findings have not been gained about filtration at low filtration pressures.

Against this backdrop, the present inventors have conducted their own studies on the filtration of protein solutions using small-pore size virus removal membranes at low filtration pressures and, surprisingly, have found that when filtration at low filtration pressures is carried out under solution conditions similar to those at high filtration pressures, viruses may be leaked into filtrates, depending on the solution conditions, resulting in protein drugs having low rates of virus removal. The present inventors have also found that filtration in the post-wash step or the stop and start step, which is also performed at low filtration pressures, may therefore have a reduced rate of virus removal, depending on the solution conditions.

On the basis of these novel findings, an object of the present invention is to provide a method for manufacturing a virus-free protein drug, comprising a step of filtering a virus-containing protein solution through a small-pore size virus removal membrane at a low filtration pressure, wherein the rate of virus removal by the method for manufacturing the virus-free protein is high.

Solution to Problem

The present inventors have conducted diligent studies to attain the object and consequently completed the present invention by finding that a protein drug having a high rate of virus removal can be obtained even at a low filtration pressure by setting the pH and salt ionic strength of a solution to be filtered to particular values.

Specifically, the present invention relates to the followings:

[1]

A method for manufacturing a virus-free protein drug, comprising the following step (a):
(a) a filtration step of filtering a virus-containing protein solution through a small-pore size virus removal membrane to obtain a virus-free protein solution,
the filtration step (a) comprising the following step (q):
(q) a low-pressure filtration step of filtering the solution through the small-pore size virus removal membrane at a filtration pressure of 0.30 kgf/cm$^2$ or lower to obtain the virus-free protein solution,
wherein the solution prior to filtration in the low-pressure filtration step (q) has a pH (X) and a salt ionic strength (Y (mM)) that satisfy the following equations 1 and 5:

$$0 \leq Y \leq 150X - 590 \quad \text{(Equation 1)}$$

$$3.5 \leq X \leq 8.0 \quad \text{(Equation 5)}$$

or the following equations 4 and 5:

$$Y = 0 \quad \text{(Equation 4)}$$

$$3.5 \leq X \leq 8.0 \quad \text{(Equation 5)}.$$

[2]

The method according to [1], wherein the solution prior to filtration in the step (q) is the virus-containing protein solution, and
wherein 50% or more of the whole virus-containing protein solution to be filtered in the filtration step (a) is filtered in the low-pressure filtration step (q).

[3]

The method according to [1], wherein the filtration step (a) is a step of filtering the virus-containing protein solution through the small-pore size virus removal membrane at a filtration pressure of 0.30 kgf/cm$^2$ or lower to obtain the virus-free protein solution, wherein the solution prior to filtration in the filtration step (a) has a pH (X) and a salt ionic strength (Y (mM)) that satisfy the following equations 1 and 5:

$$0 \leq Y \leq 150X - 590 \quad \text{(Equation 1)}$$

$$3.5 \leq X \leq 8.0 \quad \text{(Equation 5)}$$

or the following equations 4 and 5:

$$Y = 0 \quad \text{(Equation 4)}$$

$$3.5 \leq X \leq 8.0 \quad \text{(Equation 5)}.$$

[4]

The method according to [1], wherein the filtration step (a) comprises the following step (p) performed prior to the low-pressure filtration step (q): (p) a high-pressure filtration step of filtering the virus-containing protein solution through the small-pore size virus removal membrane at a filtration pressure exceeding 0.30 kgf/cm$^2$ to obtain the virus-free protein solution.

[5]

The method according to [4], wherein the solution prior to filtration in the low-pressure filtration step (q) is a buffer solution for washing.

[6]

The method according to [4] or [5], wherein the low-pressure filtration step (q) is a post-wash step or a stop and start step.

[7]

The method according to any of [1] to [6], wherein the filtration solution in the low-pressure filtration step (q) has a pH (X) and a salt ionic strength (Y (mM)) that satisfy the following equations 2 and 5:

$$0 \leq Y \leq 50X - 200 \quad \text{(Equation 2)}$$

$$3.5 \leq X \leq 8.0 \quad \text{(Equation 5)}$$

or the following equations 4 and 5:

$$Y = 0 \quad \text{(Equation 4)}$$

$$3.5 \leq X \leq 8.0 \quad \text{(Equation 5)}.$$

[8]

The method according to any of [1] to [6], wherein the solution prior to filtration in the low-pressure filtration step (q) has a pH (X) and a salt ionic strength (Y (mM)) that satisfy the following equations 3 and 5:

$$0 \leq Y \leq 50X - 250 \quad \text{(Equation 3)}$$

$$3.5 \leq X \leq 8.0 \quad \text{(Equation 5)}$$

or the following equations 4 and 5:

$$Y = 0 \quad \text{(Equation 4)}$$

$$3.5 \leq X \leq 8.0 \quad \text{(Equation 5)}.$$

[9]

The method according to any of [1] to [8], wherein the low-pressure filtration step (q) is a step of filtering the solution through the small-pore size virus removal membrane at a filtration pressure of 0.20 kgf/cm$^2$ or lower to obtain the virus-free protein solution.

[10]

The method according to any of [1] to [4], wherein a log reduction value (LRV) calculated according to the following equation 6 is 4 or higher:

$$LRV = \log_{10}(C_0/C_F) \quad \text{(Equation 6)}$$

wherein $C_0$ represents the virus concentration of the virus-containing protein solution before the filtration step (a), and $C_F$ represents the virus concentration of the virus-free protein solution after the filtration.

[11]

The method according to [5] or [6], wherein a log reduction value (LRV) calculated according to the following equation 6 is 4 or higher:

$$LRV = \log_{10}(C_0/C_F) \quad \text{(Equation 6)}$$

wherein $C_0$ represents the virus concentration of the virus-containing protein solution before the filtration step (a), and $C_F$ represents the virus concentration of the virus-free protein solution after the filtration, and LRV' calculated according to the following equation 7 is 4 or higher:

$$LRV' = \log_{10}(C_0/C_w) \quad \text{(Equation 7)}$$

wherein $C_0$ represents the virus concentration of the virus-containing protein solution before the filtration step (a), and $C_w$ represents the virus concentration of the filtrate of the buffer solution for washing after the filtration step (a).

[12]
The method according to any of [1] to [11], wherein the material of the small-pore size virus removal membrane is cellulose or a hydrophilized synthetic polymer.

[13]
The method according to any of [1] to [12], wherein the material of the small-pore size virus removal membrane is a hydrophilized synthetic polymer, and wherein the synthetic polymer is selected from the group consisting of polyvinylidene fluoride, polyether sulfone, polysulfone, and polyethylene.

[14]
The method according to any of [1] to [13], wherein the form of the small-pore size virus removal membrane is a flat membrane or a hollow fiber membrane.

[15]
The method according to any of [1] to [14], wherein the virus-containing protein solution has a protein concentration of 1 mg/mL to 100 mg/mL.

[16]
The method according to any of [1] to [15], wherein the virus-containing protein solution comprises one or more protein(s) selected from the group consisting of various monoclonal antibodies, recombinant blood coagulation factor, interferon, various hormones, various enzymes, immunoglobulin, albumin, blood coagulation factor VIII, blood coagulation factor IX, fibrinogen, and antithrombin III.

[17]
The method according to any of [1] to [15], wherein the virus-containing protein solution comprises an antibody as the protein.

[18]
The method according to any of [1] to [15], wherein the virus-containing protein solution comprises blood coagulation factor VIII or fibrinogen as the protein.

[19]
The method according to any of [1] to [18], wherein the virus-containing protein solution comprises one or more virus(es) selected from the group consisting of human parvovirus B19 (B19), minute virus of mice (MVM), porcine parvovirus (PPV), bovine parvovirus (BPV), canine parvovirus (CPV), poliovirus (Polio), circovirus, hepatitis A virus (HAV), and hepatitis E virus (HEV).

[20]
The method according to any of [1] to [19], wherein the virus-containing protein solution comprises a virus of 32 nm or smaller in diameter having no envelope.

[21]
The method according to any of [1] to [20], wherein the virus-containing protein solution comprises one or more component(s) selected from the group consisting of an inorganic salt, a buffer solution component, a surfactant, and a saccharide.

[22]
A method for manufacturing a virus-free protein drug, comprising the following step (a):
(a) a filtration step of filtering a virus-containing protein solution through a small-pore size virus removal membrane to obtain a virus-free protein solution,
the filtration step (a) comprising the following step (q):
(q) a low-pressure filtration step of filtering the solution through the small-pore size virus removal membrane at a filtration pressure of 0.30 kgf/cm² or lower to obtain the virus-free protein solution,
and comprising, prior to the low-pressure filtration step (q), a step of adjusting the solution prior to filtration so that the solution prior to filtration in the step (q) has a pH (X) and a salt ionic strength (Y (mM)) that satisfy the following equations 1 and 5:

$$0 \leq Y \leq 150X - 590 \quad \text{(Equation 1)}$$

$$3.5 \leq X \leq 8.0 \quad \text{(Equation 5)}$$

or the following equations 4 and 5:

$$Y = 0 \quad \text{(Equation 4)}$$

$$3.5 \leq X \leq 8.0 \quad \text{(Equation 5)}.$$

[23]
A virus-free protein drug obtained by a method according to any of [1] to [22].

Advantageous Effects of Invention

The present invention can provide a protein drug having a high rate of virus removal by a method for manufacturing a virus-free protein drug, comprising a step of filtering a virus-containing protein solution through a small-pore size virus removal membrane at a low filtration pressure. Thus, for example, in the case where virus-containing protein solutions are continuously filtered at a low filtration pressure, a post-wash step or a stop and start step are included, a protein drug having a high rate of virus removal can be provided.

DESCRIPTION OF EMBODIMENTS

Hereinafter, each embodiment for carrying out the present invention (hereinafter, referred to as the "present embodiment") will be described in detail. However, the present invention is not limited by the embodiments described below, and various changes or modifications can be made therein without departing from the spirit of the present invention.

A method for manufacturing a virus-free protein drug according to the present embodiment comprises a filtration step (a) of filtering a virus-containing protein solution through a small-pore size virus removal membrane to obtain a virus-free protein solution.

The "virus-containing protein solution" filtered in the step (a) is not particularly limited as long as the solution contains a protein that passes through the small-pore size virus filtration membrane described later when filtered through the filtration membrane, and may contain a virus. Particularly, a solution containing a component derived from an animal including a human, a gene, or the like as an ingredient is likely to contain a virus and as such, can be used as the virus-containing protein solution in the manufacturing method of the present embodiment to thereby efficiently provide a virus-free protein drug.

Examples of the virus-containing protein solution include solutions containing, as active ingredients, peptides or proteins that serve as ingredients for biomedicines and are manufactured using biotechnology such as genetic engineering or cell culture. Specific examples thereof include, but not limited to, solutions containing various monoclonal antibodies (IgG, IgM, etc.), recombinant blood coagulation factor, interferon, various hormones (growth hormone, erythropoietin, etc.), various enzymes, modified proteins typified by proteins with modified sugars and PEGylated proteins, and/or artificial proteins.

Further examples of the virus-containing protein solution also include ingredients for plasma derivatives that are obtained by purification from plasma. Examples of the plasma derivatives include immunoglobulin drugs, albumin drugs, and blood coagulation factor drugs. Particularly, examples of the blood coagulation factor drugs include blood coagulation factor VIII drugs, blood coagulation factor IX drugs, fibrinogen drugs, and antithrombin III drugs. Thus, specific examples of the virus-containing protein solution include, but not limited to, solutions containing immunoglobulin, albumin, and/or blood coagulation factors (blood coagulation factor VIII, blood coagulation factor IX, fibrinogen, antithrombin III, etc.). In one aspect, preferably, the virus-containing protein solution according to the present embodiment may contain an antibody as the protein. In one aspect, preferably, the virus-containing protein solution according to the present embodiment may contain blood coagulation factor VIII or fibrinogen as the protein.

The protein concentration of the virus-containing protein solution is not particularly limited as long as the concentration permits filtration through the small-pore size virus removal membrane. The protein concentration is, for example, 1 mg/mL to 100 mg/mL, preferably 1 mg/mL to 80 mg/mL, more preferably 1 mg/mL to 70 mg/mL, further preferably 1 mg/mL to 50 mg/mL. A higher protein concentration tends to slow the rate of filtration using the virus removal membrane.

Examples of the virus contained in the virus-containing protein solution include, but not particularly limited to, human parvovirus B19 (B19), minute virus of mice (MVM), porcine parvovirus (PPV), bovine parvovirus (BPV), canine parvovirus (CPV), poliovirus (Polio), circovirus, hepatitis A virus (HAV), and hepatitis E virus (HEV). Preferably, the virus is selected from the group consisting of human parvovirus B19 (B19), minute virus of mice (MVM), porcine parvovirus (PPV), bovine parvovirus (BPV), canine parvovirus (CPV), poliovirus (Polio), and hepatitis A virus (HAV).

Of these viruses, particularly, as for the parvoviruses, cases of infection by human parvovirus B19 (B19) have been reported in the field of plasma derivatives, and the European Medicines Agency (EMEA) has delivered a report about the viral safety of plasma-derived drugs. In the field of biomedicines as well, cases of contamination of monoclonal antibodies during manufacturing processes have actually occurred due to the contamination of CHO cells (mouse-derived) by mouse parvovirus. The Food and Drug Administration (FDA) has issued the Guideline on Viral Safety Evaluation of Biotechnology Products Derived from Cell Lines of Human or Animal Origin (ICH Q5A).

The parvoviruses belong to the family Parvoviridae and are the smallest viruses (diameter: 18 to 24 nm) known. Examples of the parvoviruses include human parvovirus B19 (B19), mouse parvovirus (minute virus of mice: MVM), porcine parvovirus (PPV), canine parvovirus (CPV), and bovine parvovirus (BPV).

Since the parvoviruses have no envelope, these viruses are physicochemically stable and are resistant to heat, low-pH, or chemical agent treatment, which is generally performed in an inactivation step during the process of manufacturing biological drugs. Thus, there is a growing need for parvovirus removal using virus removal membranes as a method for virus removal under a mechanism of action different from that of the inactivation method. In one aspect, the present embodiment provides a method for manufacturing a parvovirus-free protein drug.

Examples of small viruses having no envelope, other than parvoviruses, include circovirus (17 to 22 nm), hepatitis A virus (27 to 30 nm) and poliovirus (30 nm) belonging to the family Picornaviridae, and hepatitis E virus (32 nm). In one aspect, the present embodiment provides a method for manufacturing a virus-free protein drug directed to a virus having no envelope (virus having a diameter of preferably 32 nm or smaller, more preferably 30 nm or smaller, further preferably 24 nm or smaller).

The virus-containing protein solution may contain one or more component(s) selected from the group consisting of a basic amino acid, an inorganic salt, a buffer solution component, a surfactant, and a saccharide, in addition to the protein and the virus.

Examples of the basic amino acid include arginine, histidine, guanidine, lysine, and derivatives thereof, and salts of these amino acids or derivatives. The basic amino acid is preferably arginine, histidine, lysine, or a derivative thereof, or a salt of the amino acid or the derivative, more preferably arginine or a derivative thereof, or a salt of arginine or the derivative.

The inorganic salt can include NaCl and buffer salts. An acetate buffer solution, a citrate buffer solution, a phosphate buffer solution, a Tris-HCl buffer solution, or the like can be used as the buffer solution component. The concentrations of the inorganic salt and the buffer solution component can be determined with reference to a salt ionic strength described later in detail.

Examples of the surfactant include nonionic surfactants Tween 20 and Tween 80. The surfactant can be contained at a concentration of 0.01 to 0.05 wt %.

Examples of the saccharide include, but not particularly limited to, monosaccharides, disaccharides, trisaccharides, oligosaccharides, and sugar alcohols. Specifically, saccharides such as glucose, mannose, galactose, fructose, sorbose, maltose, sucrose (cane sugar), sorbitol, mannitol, and dextran can be contained alone or in combination of two or more thereof at a concentration of 1 to 10 wt %, preferably 1 to 5 wt %.

The temperature of the virus-containing protein solution prior to filtration can be set to any temperature range that does not influence the state of the protein drug to be obtained and is in the range of preferably 4° C. to 40° C., more preferably 4° C. to 35° C., from the viewpoint of preventing protein denaturation. The temperature influences the viscosity of the protein solution and also influences flux during filtration through the virus removal membrane. Thus, the temperature is further preferably in the range of 20° C. to 35° C., though differing depending on the stability of the protein itself against the temperature.

In the present embodiment, the "small-pore size virus removal membrane" used in virus removal is defined by the Parenteral Drug Association (PDA) and means a rate of removal of bacteriophage PP7 (Pseudomonas phage 7) having a particle size of 30 to 33 nm by a membrane is larger than 4 $\log_n$ measured on the basis of the approach described in PDA Technical Report 41 (revised in 2008, Appendix 1).

Alternatively, the small-pore size virus removal membrane is defined by PDA as a membrane that has a rate of protein permeation or recovery larger than 90% tested by an approach similar to that for the bacteriophage PP7 using an aqueous intravenous immunoglobulin (IVIG) solution or an IVIG-containing buffer solution. The rate of protein permeation is represented by the ratio of the protein concentration of a solution after membrane filtration to the protein concentration of a solution prior to filtration and measured after membrane filtration of a solution in a sufficient volume until the protein concentration of the solution after membrane filtration is stabilized. The protein concentration can be measured using UV spectrometry ($A_{280}$).

Desirably, the small-pore size virus removal membrane has LRV of 4 or higher calculated according to the equation 6 described later as to parvovirus removal performance at a recommended pressure for each virus removal membrane.

The material of the small-pore size virus removal membrane is preferably cellulose or a hydrophilized synthetic polymer. Regenerated cellulose, natural cellulose, cellulose acetate, or the like can be used as the cellulose. Hydrophilized polyvinylidene fluoride (PVDF), hydrophilized polyether sulfone (PES), hydrophilized polyethylene (PE), hydrophilized polysulfone (PS), or the like can be used as the hydrophilized synthetic polymer. Examples of the method for hydrophilization include: methods for introducing hydrophilic functional groups to membrane surface by a method such as coating, graft reaction, or cross-linking reaction; and methods for immobilizing hydrophilic polymers to membrane surface.

The form of the membrane may be any of a flat membrane and a hollow fiber membrane. However, a hollow fiber membrane is preferred, since it is possible to miniaturize a formed membrane by loading the membrane to a container, even though the membrane has a large area. A filter can be prepared so that its space is partitioned by the membrane into primary space on the entrance side of a solution to be filtered and a secondary space on the filter exit side. For use in filtration, the virus removal membrane can be used in a filter form.

Examples of commercially available small-pore size virus removal membranes directed to the removal of small viruses such as parvoviruses include: Planova (registered trademark) 15N (manufactured by Asahi Kasei Medical Co., Ltd.) and Planova (registered trademark) 20N (manufactured by Asahi Kasei Medical Co., Ltd.) made of cellulose; Planova (registered trademark) BioEX (manufactured by Asahi Kasei Medical Co., Ltd.), Ultipore (registered trademark) VF DV20 (manufactured by Pall Corp.), and Viresolve NFP (manufactured by EMD Millipore Corp.) made of hydrophilized PVDF; and Virosart CPV (manufactured by Sartorius K.K.) and Viresolve Pro (manufactured by EMD Millipore Corp.) made of hydrophilized PES. The virus removal membrane can be appropriately selected according to the type of the virus to be removed or the protein drug to be manufactured.

The filtration of the virus-containing protein solution through the small-pore size virus removal membrane can be performed by a usual method for using each small-pore size virus removal membrane. The filtration is preferably dead-end filtration from the viewpoint of its high rate of recovery. Any filtration method may be used, including constant-pressure filtration in which the filtration pressure is kept constant, filtration in which the filtration pressure is varied, constant-rate filtration in which the rate of filtration is kept constant, etc. A preferable filtration method is adopted according to the composition of the solution prior to filtration.

The range of the filtration pressure in the step (a) is below the resisting pressure of the small-pore size virus removal membrane, though differing depending on the material of the membrane. In the case of, for example, a small-pore size virus removal membrane made of cellulose, the optimum filtration pressure is in the range of 0.00 kgf/cm² (0.0 kPa) to 1.00 kgf/cm² (9.8×10 kPa). In the case of a small-pore size virus removal membrane made of hydrophilized PVDF, hydrophilized PES, or hydrophilized PS, the optimum filtration pressure is in the range of 0.00 kgf/cm² (0.0 kPa) to 5.00 kgf/cm² (4.9×10² kPa).

In the manufacturing method of the present embodiment, the step (q) is a low-pressure filtration step of filtering the solution through the small-pore size virus removal membrane at a filtration pressure of 0.30 kgf/cm² or lower to obtain the virus-free protein solution. This step is included in the step (a). Specifically, the step (q) refers to a step of performing filtration at a filtration pressure of 0.30 kgf/cm² or lower in the step (a).

The filtration of a virus-containing solution using a virus removal membrane is usually performed at a filtration pressure as high as possible in order to treat larger amounts of protein solutions in a short time. The present inventors, however, have found that such a low-pressure filtration step of filtering a virus-containing solution through the small-pore size virus removal membrane at a low filtration pressure may fail to remove viruses due to their leakage into filtrates. The present inventors have further found that in such a low-pressure filtration step, the pH (X) and salt ionic strength (Y (mM)) of the solution prior to filtration can be adjusted so that X and Y satisfy the equations 1 and 5 or the equations 4 and 5 shown below to thereby obtain a virus-free filtrate without leaking viruses into filtrates.

In the present embodiment, the filtration pressure can be easily measured using a pressure gauge disposed in a virus removal apparatus equipped with the small-pore size virus removal membrane. Alternatively, a pressure gauge may be placed on the feed solution container side and used in measurement. Depending on the composition of the solution prior to filtration, viruses are leaked into filtrates at a filtration pressure of 0.30 kgf/cm² or lower (e.g., around 0.20 kgf/cm² as shown in Examples described later). Without being limited by the theory, this is probably because: a lower filtration pressure weakens the ability of the small-pore size virus removal membrane to retain viruses and instead increases the degree of freedom of viruses, which are in turn leaked into filtrates; and particularly, this phenomenon becomes obvious at the filtration pressure of 0.30 kgf/cm² or lower.

However, in the low-pressure filtration step, a virus-free filtrate can be obtained if the solution prior to filtration has a pH (X) and a salt ionic strength (Y (mM)) that satisfy the following equations 1 and 5:

$$0 \leq Y \leq 150X - 590 \qquad \text{(Equation 1)}$$

$$3.5 \leq X \leq 8.0 \qquad \text{(Equation 5)}$$

or the following equations 4 and 5:

$$Y = 0 \qquad \text{(Equation 4)}$$

$$3.5 \leq X \leq 8.0 \qquad \text{(Equation 5).}$$

Preferably, the solution prior to filtration in the low-pressure filtration step may have a pH (X) and a salt ionic strength (Y (mM)) that satisfy the following equations 2 and 5:

$$0 \leq Y \leq 50X - 200 \qquad \text{(Equation 2)}$$

$$3.5 \leq X \leq 8.0 \qquad \text{(Equation 5)}$$

or the following equations 4 and 5:

$$Y = 0 \qquad \text{(Equation 4)}$$

$$3.5 \leq X \leq 8.0 \qquad \text{(Equation 5)}$$

according to the rate of virus removal in the protein drug to be obtained. Particularly preferably, the solution prior to filtration in the low-pressure filtration step may have a pH (X) and a salt ionic strength (Y (mM)) that satisfy the following equations 3 and 5:

$$0 \leq Y \leq 50X - 250 \quad \text{(Equation 3)}$$

$$3.5 \leq X \leq 8.0 \quad \text{(Equation 5)}$$

or the following equations 4 and 5:

$$Y = 0 \quad \text{(Equation 4)}$$

$$3.5 \leq X \leq 8.0 \quad \text{(Equation 5)}.$$

As shown in Examples described later, the present inventors have confirmed that, if a filtration pressure is 0.30 kgf/cm² or lower, for example, around 0.20 kgf/cm² (e.g., 0.10 kgf/cm² to 0.30 kgf/cm² and as a further example, 0.15 kgf/cm² to 0.25 kgf/cm²) and the pH (X) and salt ionic strength (Y (mM)) of the solution prior to filtration satisfy the equation 1, the rate of virus removal is high.

The rate of virus removal by filtration can be indicated by a log reduction value (LRV). LRV is calculated according to the following equation 6:

$$LRV = \log_{10}(C_0/C_F) \quad \text{(Equation 6)}$$

wherein $C_0$ represents the virus concentration of the solution prior to filtration, and $C_F$ represents the virus concentration of the filtered solution. A lower LRV value represents a lower rate of virus removal.

Each virus concentration in the calculation of LRV can be indicated by an infectivity titer, the copy number of viral nucleic acids, etc. Examples of methods for measuring the infectivity titer include TCID50 and plaque methods. The copy number of viral nucleic acids can be measured using, for example, PCR.

In general, LRV of 4 or higher in the evaluation of virus removal membrane performance means that viruses are sufficiently removed by the membrane filtration. Likewise, LRV of 5 or higher means that viruses are removed to 1/10⁵ or less. LRV of 6 or higher means that viruses are removed to 1/10⁶ or less and rarely leaked into filtrates.

In the present embodiment, LRV calculated according to the equation 6 from the virus concentration ($C_0$) of the virus-containing protein solution before the filtration step (a) and the virus concentration ($C_F$) of the virus-free protein solution after the filtration is preferably 4 or higher, more preferably 5 or higher, further preferably 6 or higher. A virus concentration ($C_F$) equal to or lower than the detection limit is also preferred.

As is evident from the results of Examples described later, a lower pH of the solution prior to filtration in the low-pressure filtration step increases virus leakage into filtrates and decreases LRV. This phenomenon becomes more obvious in the presence of a higher salt ionic strength of the solution prior to filtration. The largest virus leakage into filtrates is seen when the solution prior to filtration has a low pH and a high salt ionic strength.

As shown in Examples described later, the low-pressure filtration step can be performed with a rate of virus removal (LRV) of 4 or higher when the pH (X) and salt ionic strength (Y (mM)) of the solution prior to filtration satisfy either combination of the equations 1 and 5 or the equations 4 and 5. By contrast, viruses are leaked into filtrates due to a low rate of virus removal when X and Y do not satisfy any combination of the equations 1 and 5 or the equations 4 and 5. Furthermore, the low-pressure filtration step can be performed with a rate of virus removal (LRV) of 5 or higher when X and Y satisfy either combination of the equations 2 and 5 or the equations 4 and 5. The low-pressure filtration step can be performed with a higher rate of virus removal that achieves a virus concentration equal to or lower than the detection limit in the filtrate when X and Y satisfy either combination of the equations 3 and 5 or the equations 4 and 5. Thus, the pH (X) and salt ionic strength (Y (mM)) of the solution prior to filtration can be adjusted so that X and Y satisfy the combination of the equations as described above to thereby obtain a virus-free solution without leaking viruses into filtrates even at a low filtration pressure.

In the low-pressure filtration step, the pH (X) of the solution prior to filtration is desirably 3.5 or higher and 8.0 or lower, more preferably 4.0 or higher and 8.0 or lower. At a pH lower than 3.5 or exceeding 8.0, the protein may be denatured or degraded.

The salt ionic strength (Y (mM)) of the solution prior to filtration is obtained by calculating the product of the concentration of ion by its charge square for each of the all ionic species derived from salts released in the solution, summing the products and further calculating half of the summed products, and is represented by the following formula 8:

$$Y = \tfrac{1}{2}\Sigma(C_i \times Z_i^2) \quad \text{(Equation 8)}$$

wherein $C_i$ represents the mol concentration of each ion, and $Z_i$ represents the charge number of each ion.

Examples of the salt-derived ionic species include ions derived from inorganic salts and ions derived from salts constituting buffer solution components. In the case of a solution containing no buffer solution component and containing only an inorganic salt, its salt ionic strength can be calculated as the ionic strength of only the inorganic salt. When the inorganic salt is NaCl, the salt ionic strength is identical to the salt concentration of NaCl.

Typically, in the solution containing the buffer solution component, the buffer solution component plays a role in adjusting the pH. The salt ionic strength is often adjusted by adding an inorganic salt (e.g., NaCl).

In the low-pressure filtration step, the salt ionic strength (Y (mM)) of the solution prior to filtration is desirably in the range of 500 mM or lower that neither denatures the protein nor influences the formation of aggregates. Y is preferably 300 mM or lower, more preferably 150 mM or lower.

In one aspect of the present embodiment, the low-pressure filtration step can also be performed with a high rate of virus removal when the pH (X) and salt ionic strength (Y (mM)) of the solution prior to filtration are in the following ranges:

$3.5 \leq X < 4$ and $Y = 0$;

$4 \leq X < 4.6$ and $0 \leq Y \leq 50$, preferably $0 \leq Y \leq 10$, more preferably $Y = 0$;

$4.6 \leq X < 5$ and $0 \leq Y \leq 100$, preferably $0 \leq Y \leq 50$, more preferably $0 \leq Y \leq 10$, further preferably $Y = 0$;

$5 \leq X < 6$ and $0 \leq Y \leq 150$, preferably $0 \leq Y \leq 100$, more preferably $0 \leq Y \leq 50$, further preferably $Y = 0$; and $6 \leq X \leq 8$ and $0 \leq Y \leq 300$, preferably $0 \leq Y \leq 150$, more preferably $0 \leq Y \leq 100$.

The pH of the solution prior to filtration can be adjusted by the selection and increase or decrease in the amount of a buffer solution component such as an acetate buffer solution, a citrate buffer solution, a phosphate buffer solution, or a Tris-HCl buffer solution, by the addition of an alkali such as NaOH, or by the addition of an acid such as HCl. The salt ionic strength of the solution prior to filtration can be adjusted by increase or decrease in the amount of a salt such as NaCl or a buffer salt. Also, the pH and salt ionic strength of the solution prior to filtration can be measured by an approach known by those skilled in the art.

The solution prior to filtration that is filtered in the step (q) is not particularly limited as long as the solution prior to filtration has a pH (X) and a salt ionic strength (Y (mM)) that satisfy the equations 1 and 5 or the equations 4 and 5. Examples thereof include the virus-containing protein solutions described above as well as buffer solutions (e.g., a buffer solution for washing described later) and water. The composition of the buffer solutions is not particularly limited. The buffer solutions may contain any of the buffer solution components described above as well as any of the basic amino acids, inorganic salts, surfactants, saccharides, etc. described above. Preferably, the solution prior to filtration contains a component overlapping with that in the virus-containing protein solution in the step (a).

In one aspect of the present embodiment, the solution prior to filtration in the step (q) is the virus-containing protein solution, wherein 50% or more of the whole virus-containing protein solution to be filtered in the filtration step (a) is filtered in the low-pressure filtration step (q).

In general, the filtration of a virus-containing protein solution using a small-pore size virus filtration membrane is performed at a filtration pressure as high as possible in order to enhance treatment efficiency. However, filtration at a low filtration pressure is preferred for some proteins. One example of such proteins includes an antibody. Examples of the antibody include monoclonal antibodies and polyclonal antibodies.

In the case of a virus-containing protein solution containing such a protein, desirably, 50% or more, preferably 75% or more, more preferably 90% or more, further preferably 95% or more of the whole virus-containing protein solution to be filtered in the filtration step (a) is filtered in the low-pressure filtration step (q).

In one aspect of the present embodiment, all of the whole virus-containing protein solution to be filtered in the filtration step (a) may be filtered in the low-pressure filtration step (q). In such a case, the filtration step (a) is a step of filtering the virus-containing protein solution through the small-pore size virus removal membrane at a filtration pressure of 0.30 kgf/cm$^2$ or lower to obtain the virus-free protein solution, wherein the solution prior to filtration in the filtration step (a) has a pH (X) and a salt ionic strength (Y (mM)) that satisfy the following equations 1 and 5:

$0 \leq Y \leq 150X - 590$ (Equation 1)

$3.5 \leq X \leq 8.0$ (Equation 5)

or the following equations 4 and 5:

$Y = 0$ (Equation 4)

$3.5 \leq X \leq 8.0$ (Equation 5).

In this case, the filtration pressure and the equations 1, 4, and 5 are as described about the step (q). The virus-containing protein solution suitable for such filtration is a monoclonal antibody solution.

In one aspect of the present embodiment, the filtration step (a) comprises the following step (p) performed prior to the low-pressure filtration step (q): (p) a high-pressure filtration step of filtering the virus-containing protein solution through the small-pore size virus removal membrane at a filtration pressure exceeding 0.30 kgf/cm$^2$ to obtain the virus-free protein solution. The step (p) is included, as in the step (q), in the step (a) and refers to a step of performing filtration at a filtration pressure higher than 0.30 kgf/cm$^2$ in the step (a).

The small-pore size virus removal membrane, the virus-containing protein solution, and the filtration method in the step (p) are as described about the step (a).

The filtration pressure in the step (p) differs depends on the material of the small-pore size virus removal membrane, but is not particularly limited as long as the filtration pressure is higher than 0.30 kgf/cm$^2$ and is in the range of pressures equal to or lower than the resisting pressure of the membrane. In the case of, for example, a small-pore size virus removal membrane made of cellulose, the optimum filtration pressure is in the range of 0.50 kgf/cm$^2$ (4.9×10 kPa) to 1.00 kgf/cm$^2$ (9.8×10 kPa). In the case of a small-pore size virus removal membrane made of hydrophilized PVDF, hydrophilized PES, or hydrophilized PS, the optimum filtration pressure is in the range of 1.00 kgf/cm$^2$ (9.8×10 kPa) to 5.00 kgf/cm$^2$ (4.9×10$^2$ kPa).

The continuous filtration (which is performed at a filtration pressure as high as possible in order to enhance treatment efficiency) of virus-containing protein solutions using a small-pore size virus filtration membrane may leave protein particles inside the membrane (on a side opposite to the filtrate) with increase in the amount of the solution filtered, resulting in clogging. Thus, operation called a post-wash step may be performed in which the proteins remaining inside the membrane are washed off into filtrates by the filtration of a protein-free solution (washing solution). In the present embodiment, the post-wash step refers to filtration added after protein filtration in order to recover proteins remaining inside the small-pore size virus removal membrane. In the case of performing the post-wash step, a line to which the solution prior to filtration is introduced is switched because the washing solution is filtered instead of the protein-containing solution. If the filtration pressure is kept high during this line switching, the solution flows backward to the washing solution side. Thus, the filtration pressure is temporarily relieved to 0.0 kPa. After the line switching, the filtration pressure is applied again to filter the washing solution. The time period from the pressure drop to zero to the restart of filtration of the washing solution under filtration pressure is not particularly limited. A sufficient pressure drop occurs after, for example, 5 seconds or longer. A more sufficient pressure drop occurs after 1 minute or longer, 5 minutes or longer, or 30 minutes or longer. From the viewpoint of workability, the filtration is often restarted, for example, within 7 days, within 5 days, within 3 days, or within 24 hours. Since the filtration pressure is temporarily decreased during the line switching, viruses are leaked into filtrates, depending on the composition of the solution prior to filtration. This virus leakage can be prevented by the step (q) as mentioned above.

Specifically, in one aspect of the present embodiment, protein particles remaining inside the membrane during the course of the step (p) are washed off by the post-wash step including the low-pressure filtration step (q). When the low-pressure filtration step (q) is (included in) the post-wash step, the solution prior to filtration in the step (q) is preferably a protein-free washing solution. The composition of the washing solution is not particularly limited. Preferably, the washing solution contains a component overlapping with that in the virus-containing protein solution in the step (a) or (p) and is more preferably a buffer solution for washing. The buffer solution for washing is a buffer solution used for dissolving proteins in the manufacture of the virus-containing protein solution for use in the step (a). The post-wash step can be performed two or more times, if necessary.

When the step (a) comprises the post-wash step, preferably, LRV calculated according to the equation 6 from the virus concentration ($C_0$) of the virus-containing protein solution before the filtration step (a) and the virus concentration ($C_F$) of the virus-free protein solution after the filtration is 4 or higher (preferably 5 or higher), and LRV' calculated according to the following equation 7 is 4 or higher (preferably 5 or higher):

$$\text{LRV'} = \log_{10}(C_0/C_w) \qquad \text{(Equation 7)}$$

wherein $C_0$ represents the virus concentration of the virus-containing protein solution before the filtration step (a), and $C_w$ represents the virus concentration of the filtrate of the buffer solution for washing after the filtration step (a). The virus concentration can be measured using the approach described above about the equation 6.

In the equation 7, the virus concentration ($C_w$) of the filtrate of the buffer solution for washing after the filtration step (a) refers to the virus concentration of only the filtrate of the buffer solution for washing filtered in the post-wash step. Viruses derived from the virus-containing protein solution filtered before the post-wash step may remain inside the small-pore size virus filtration membrane. In the post-wash step involving filtration at a low filtration pressure, the viruses may be leaked into the filtrate of the buffer solution for washing, depending on the pH and salt ionic strength of the solution prior to filtration. The pH (X) and salt ionic strength (Y (mM)) of the solution prior to filtration can be adjusted so that X and Y satisfy the equations 1 and 5 or the equations 4 and 5 to thereby prevent this virus leakage even in the post-wash step.

Examples of such decrease in filtration pressure during filtration through a virus removal membrane, as in the post-wash step, include a step involving a case in which pressurization is suspended during filtration and then restarted (stop and start step). A possible example is a case in which a filtration pressure is stopped for a reason such as power off during the filtration of a virus-containing protein solution through a small-pore size virus filtration membrane and then applied again by power on. The time period from the pressure drop to zero to the restart of filtration of the washing solution under filtration pressure is not particularly limited. A sufficient pressure drop occurs after, for example, 5 seconds or longer. A more sufficient pressure drop occurs after 1 minute or longer, 5 minutes or longer, or minutes or longer. From the viewpoint of workability, the filtration is often restarted, for example, within 7 days, within 5 days, within 3 days, or within 24 hours. Since the filtration pressure is also temporarily decreased in such a case, viruses may be leaked into filtrates, depending on the composition of the solution prior to filtration. This virus leakage can be prevented by the step (q) as mentioned above.

Specifically, in one aspect of the present embodiment, a virus-free protein solution can be reliably obtained by the low-pressure filtration step (q) in which the pH (X) and salt ionic strength (Y (mM)) of the solution prior to filtration fall within the predetermined ranges, even if the filtration pressure is decreased during the step (p).

In one aspect of the present embodiment, if the filtration step (a) comprises the step (p) performed prior to the low-pressure filtration step (q), the filtration pressure in the step (q) might become almost 0.0 kPa. The filtration pressure may become almost 0.0 kPa, for example, when a line to which the solution prior to filtration is introduced is switched in the post-wash step or when power is turned off in the stop and start step. In this case, the pressurization may be restarted by: closing the line between the small-pore size virus removal membrane and a container for feed of the solution prior to filtration; then setting the pressure on the feed container side to the optimum filtration pressure described about the step (a); and then opening the line between the small-pore size virus removal membrane and the container for feed of the solution prior to filtration, followed by filtration at a constant pressure, or opening the line between the small-pore size virus removal membrane and the container for feed of the solution prior to filtration, followed by filtration with the pressure gradually increased to the predetermined value. For example, the time period over which the filtration pressure is left out until becoming 0.0 kPa (duration of filtration performed at a low filtration pressure) is 3 hours, and then, pressurization may be restarted to perform filtration. With the rate of virus removal by this filtration as a guideline, a time period shorter than 3 hours over which the filtration pressure is left out is presumed to offer a higher rate of virus removal than that offered by a time period of 3 hours.

In the method for manufacturing a virus-free protein drug according to the present embodiment, preliminary filtration through a membrane filter having a pore size larger than that of the small-pore size virus removal membrane may be performed prior to the step (a). In this context, Planova (registered trademark) 35N, Planova (registered trademark) 75N (both manufactured by Asahi Kasei Medical Co., Ltd.), a 0.1-μm filter, 0.2-μm filter, or the like can be used as the filter having a larger pore size. The step (a) may be directly performed using the small-pore size virus removal membrane without the preliminary filtration.

Any one or more of chromatography treatment, S/D treatment, concentration treatment, and concentration and buffer replacement treatment may be performed prior to the step (a).

Examples of the chromatography treatment can include column chromatography using a column packed with an ion-exchange resin or gel filtration resin, and membrane chromatography using a porous membrane having an ion-exchange group added to the surface. Examples of the separation mode of chromatography include gel filtration chromatography, ion-exchange chromatography (cation-exchange: CEX, anion-exchange: AEX), hydrophobic interaction chromatography (HIC), affinity chromatography, metal chelate affinity chromatography, and hydroxyapatite chromatography. Chromatography using ion-exchange and hydrophobic interaction chromatography ligands in combination may be used.

The S/D treatment can be performed by virus inactivation according to a method known in the art using an organic solvent such as tri-n-butyl phosphate (TNBP) and a surfactant such as Tween 80.

The concentration treatment can be performed according to a method known in the art using an ultrafiltration (UF) membrane. This treatment can be performed by centrifugal concentration.

The buffer replacement treatment may be performed simultaneously with concentration according to a method known in the art using an ultrafiltration membrane. This treatment may be performed by gel filtration. Alternatively, the treatment can also be performed by dialysis using a dialysis membrane.

Subsequently to the step (a), the obtained virus-free protein solution can be purified by chromatography treatment. Also, the virus-free protein solution can be further concentrated by UF treatment. The virus-free protein solution obtained in the step (a) or its purified or concentrated product may be used as a final drug with its liquid composition unchanged. Alternatively, the virus-free protein solution obtained in the step (a) or its purified or concentrated product may be supplemented with a saccharide, a surfactant, or the like and used as a final drug. The buffer in the solution may be replaced with a solvent of composition different therefrom. Also, the solution may be freeze-dried.

In one aspect, the present embodiment also relates to a method for manufacturing a virus-free protein drug, comprising the following step (a):

(a) a filtration step of filtering a virus-containing protein solution through a small-pore size virus removal membrane to obtain a virus-free protein solution, the filtration step (a) comprising the following step (q):

(q) a low-pressure filtration step of filtering the solution through the small-pore size virus removal membrane at a filtration pressure of 0.30 kgf/cm² or lower to obtain the virus-free protein solution, and comprising, prior to the low-pressure filtration step (q), a step of adjusting the solution prior to filtration so that the solution prior to filtration in the step (q) has a pH (X) and a salt ionic strength (Y (mM)) that satisfy the following equations 1 and 5:

$0 \leq Y \leq 150X - 590$ (Equation 1)

$3.5 \leq X \leq 8.0$ (Equation 5)

or the following equations 4 and 5:

$Y = 0$ (Equation 4)

$3.5 \leq X \leq 8.0$ (Equation 5).

The present embodiment also relates to a virus-free protein drug obtained by the manufacturing method. The present embodiment also relates to a method for removing a virus in a virus-containing protein solution, comprising performing the step (a) (comprising the step (q)).

EXAMPLES

Hereinafter, the present invention will be described with reference to Examples. However, the scope of the present invention should be interpreted without being limited by Examples below.

In Examples shown below, a hollow fiber membrane Planova (registered trademark) 20N (manufactured by Asahi Kasei Medical Co., Ltd.) made of cellulose was used as the small-pore size virus removal membrane used. A pH was measured using a pH meter. A salt ionic strength was calculated from the amount of a salt (salt concentration) used for adjusting each solution.

(i) Preparation of Protein Solution

Polyclonal antibodies (human IgG) (Venoglobulin-1H, manufactured by Benesis Corp.) were used. The antibodies were diluted with injectable water (Otsuka Pharmaceutical Co., Ltd.) to an antibody concentration of 10 mg/mL. The salt ionic strength of each solution was adjusted to a value shown in each Example below using a 1 M aqueous NaCl solution. The pH was adjusted to a value shown in each Example below using 0.1 M HCl or 0.1 M NaOH.

(ii) Measurement of Rate of Virus Removal (LRV)

Cultured PK-13 cells (obtained from ATCC; ATCC No. CRL-6489) were diluted with D-MEM (manufactured by Invitrogen Corp., high-glucose) containing 3 vol % of bovine serum (manufactured by EMD Millipore Corp. (Upstate); used after being inactivated by heating for 30 minutes in a water bath of 56° C.) and 1 vol % of penicillin/streptomycin (+10000 units/mL penicillin, +10000 µg/mL Streptomycin; manufactured by Invitrogen Corp.) (hereinafter, this mixed solution is referred to as "3% FBS/D-MEM") to prepare a diluted suspension having a cell concentration of $2.0 \times 10^5$ cells/mL. Ten 96-well round-bottom cell culture plates (manufactured by Becton, Dickinson and Company (BD Falcon)) were prepared, and this cell suspension was dispensed at a concentration of 100 µL/well to all wells.

Subsequently, a filtrate obtained by filtration in each Example below was diluted with 3% FBS/D-MEM to prepare 10-fold, $10^2$-fold, $10^3$-fold, $10^4$-fold, and $10^5$-fold dilutions. Each unfiltered solution (virus-containing protein solution) collected immediately before filtration was diluted with 3% FBS/D-MEM to prepare $10^2$-fold, $10^3$-fold, $10^4$-fold, $10^5$-fold, $10^6$-fold, and $10^7$-fold dilutions. Each filtrate and the 10-fold, $10^2$-fold, $10^3$-fold, $10^4$-fold, and $10^5$-fold dilutions of the filtrate as well as the $10^2$-fold, $10^3$-fold, $10^4$-fold, $10^5$-fold, $10^6$-fold, and $10^7$-fold dilutions of the unfiltered solution were separately dispensed at a concentration of 100 µL/well to 8 wells of the 96-well cell culture plates to which the cell suspension was dispensed. The cells were cultured at 37° C. for 10 days in a 5% $CO_2$ atmosphere in an incubator.

Subsequently, the cell culture plates after the 10-day culture were subjected to TCID50 (50% infectivity titer) measurement by the erythrocyte adsorption method (see Virus Jikken Gaku (Experimental Study of Viruses in English), General, Ed., National Institute of Infectious Diseases, p. 173). Preserved chicken blood (manufactured by Nippon Bio-Test Laboratories Inc.) was diluted 5-fold with PBS (−) (manufactured by Nissui Pharmaceutical Co., Ltd.; prepared by the method described in the instruction attached to the product) and then centrifuged at 2500 rpm at 4° C. for 5 minutes to precipitate erythrocytes. Then, the supernatant was removed by aspiration. The obtained erythrocyte-containing precipitates were diluted again 200-fold with the PBS (−).

Subsequently, the PBS (−) dilution of the prepared erythrocyte precipitates was dispensed at a concentration of 100 µL/well to all the wells of the cell culture plates and left standing for 2 hours. Then, the presence or absence of the adsorption of erythrocytes to the surface of the cultured cellular tissue was visually confirmed. Wells confirmed to have the adsorption were counted as those with viral infection, whereas wells confirmed to have no such adsorption were counted as those without viral infection. As for the presence or absence of viral infection in each obtained culture solution, the percentage was confirmed on the basis of each filtrate or each of its dilutions, or each dilution of the unfiltered solution. $Log(TCID_{50}/mL)$ was calculated as an infectivity titer by the Reed-Muench method (see Virus Jikken Gaku (Experimental Study of Viruses in English), General, Ed., National Institute of Infectious Diseases, p. 479-480). The rate of virus removal (LRV) was calculated according to the following equation:

$LRV = \log_{10}(C_0/C_F)$ wherein $C_0$ represents the infectivity titer of the unfiltered solution (virus-containing protein solution) before filtration through the small-pore size virus removal membrane; and $C_F$ represents the infectivity titer of the solution filtered through the small-pore size virus removal membrane.

Example 1

Filtration Using Virus Removal Membrane at Different Filtration Pressures

Each protein solution (polyclonal antibody solution) having a pH of 4, 4.6, 5, 6, 7, or 8 and a salt ionic strength fixed to 100 mM was prepared by the method described above in (i) (Experimental Examples 1 to 16). Then, porcine parvovirus (PPV; Japanese Association of Veterinary Biologics; the same holds true for Examples 2 to 4 below) was added at a concentration of 0.5 vol % to each solution, and the mixture was well stirred into a virus-containing protein solution.

Each solution thus obtained was subjected to dead-end filtration through a small-pore size virus removal membrane (Planova (registered trademark) 20N) having a membrane area of 0.001 m² at a filtration pressure of 0.10, 0.20, 0.50, or 0.80 kgf/cm² until the amount of the solution filtered reached 50 L/m². The filtration pressure was measured using a pressure gauge placed on the feed solution container side. The rate of PPV removal in the 50 L/m² pool was measured by the method described above in (ii).

The relationship of each filtration pressure and each pH with the rate of virus removal (LRV) is shown in Table 1 below. As shown in Table 1, even though pH varied, the rate of virus removal was kept high even in the case of a high filtration pressure. By contrast, a lower pH of the virus-containing protein solution prior to filtration was shown to produce a lower rate of virus removal in the case of a low filtration pressure, resulting in virus leakage.

TABLE 1

|  | pH | Salt ionic strength (mM) | Filtration pressure (kgf/cm²) | LRV |
| --- | --- | --- | --- | --- |
| Experimental Example 1 | 4.0 | 100 | 0.80 | ≥5.92 |
| Experimental Example 2 | 5.0 | 100 | 0.80 | ≥6.00 |
| Experimental Example 3 | 6.0 | 100 | 0.80 | ≥5.59 |
| Experimental Example 4 | 7.0 | 100 | 0.80 | ≥5.78 |
| Experimental Example 5 | 4.0 | 100 | 0.50 | ≥5.87 |
| Experimental Example 6 | 5.0 | 100 | 0.50 | ≥5.83 |
| Experimental Example 7 | 6.0 | 100 | 0.50 | ≥6.00 |
| Experimental Example 8 | 7.0 | 100 | 0.50 | ≥5.84 |
| Experimental Example 9 | 4.0 | 100 | 0.20 | 3.88 |
| Experimental Example 10 | 5.0 | 100 | 0.20 | 4.69 |
| Experimental Example 11 | 6.0 | 100 | 0.20 | 5.17 |
| Experimental Example 12 | 7.0 | 100 | 0.20 | ≥5.34 |
| Experimental Example 13 | 4.0 | 100 | 0.10 | 3.50 |
| Experimental Example 14 | 5.0 | 100 | 0.10 | 4.40 |
| Experimental Example 15 | 6.0 | 100 | 0.10 | 5.00 |
| Experimental Example 16 | 7.0 | 100 | 0.10 | ≥5.34 |

Example 2

Continuous Low-pressure Filtration of Virus-containing Protein Solutions Differing in pH and Salt Ionic Strength Each protein solution (polyclonal antibody solution) having any of the pHs and salt ionic strengths of Experimental Examples 17 to 31 shown in Table 2 was prepared by the method described above in (i). Then, porcine parvovirus (PPV) was added at a concentration of 0.5 vol % to each solution, and the mixture was well stirred to obtain a virus-containing protein solution.

Each solution thus obtained was subjected to dead-end filtration through a small-pore size virus removal membrane (Planova (registered trademark) 20N) having a membrane area of 0.001 m² at a filtration pressure of 0.20 kgf/cm² (2.0×10 kPa) until the amount of the solution filtered reached 50 L/m². The filtration pressure was measured using a pressure gauge placed on the feed solution container side. The rate of PPV removal (LRV) in the 50 L/m² pool was measured by the method described above in (ii). The results are shown in Table 2.

As shown in Table 2, the rate of virus removal was shown to be high without leaking viruses into filtrates, depending on the salt ionic strength, even in the case of a low filtration pressure and a low pH of the virus-containing protein solution prior to filtration.

TABLE 2

|  | pH | Salt ionic strength (mM) | LRV |
| --- | --- | --- | --- |
| Experimental Example 17 | 4.0 | 0 | ≥5.92 |
| Experimental Example 18 | 4.0 | 10 | 4.67 |
| Experimental Example 19 | 4.0 | 100 | 3.88 |
| Experimental Example 20 | 4.6 | 0 | ≥5.17 |
| Experimental Example 21 | 4.6 | 100 | 4.74 |
| Experimental Example 22 | 5.0 | 0 | ≥6.22 |
| Experimental Example 23 | 5.0 | 10 | 5.37 |
| Experimental Example 24 | 5.0 | 50 | 5.14 |
| Experimental Example 25 | 5.0 | 100 | 4.69 |
| Experimental Example 26 | 6.0 | 0 | ≥6.00 |
| Experimental Example 27 | 6.0 | 100 | 5.17 |
| Experimental Example 28 | 7.0 | 0 | ≥6.00 |
| Experimental Example 29 | 7.0 | 100 | ≥5.34 |
| Experimental Example 30 | 8.0 | 0 | ≥6.00 |
| Experimental Example 31 | 8.0 | 100 | ≥5.50 |

Figure 1:
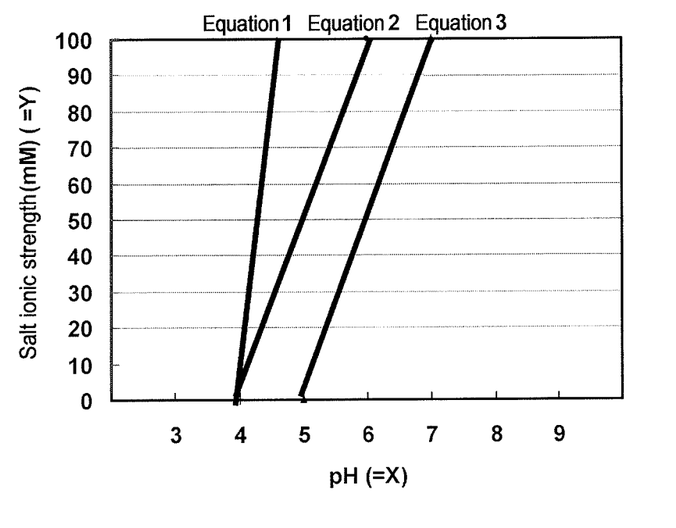
FIG. 1 is a graph showing the relationship between the pH (X) and salt ionic strength (Y (mM)) of a solution prior to filtration in the absence of virus leakage in Example 2. Lines corresponding to the equations 1, 2, and 3 determined in Example 2 are indicated from left to right.

The results shown in Table 2 also demonstrated that the filtration of the virus-containing protein solution through the small-pore size virus removal membrane at a low filtration pressure exhibited the correlation between the pH (X) and salt ionic strength (Y (mM)) of the solution in the absence of virus leakage. Relational equations shown below are given for the pH (X) and salt ionic strength (Y (mM)) of the solution prior to filtration. The relationship between X and Y shown in the equations 1 to 3 shown below is illustrated in FIG. 1.

The ranges of X and Y that achieve LRV of 4 or higher satisfy the following equation 1 or 4 (based on the results of Experimental Example 18 (pH: 4, salt ionic strength: 10 mM) and Experimental Example 21 (pH: 4.6, salt ionic strength: 100 mM)):

$$0 \le Y \le 150X - 590 \quad \text{(Equation 1)}$$

$$Y = 0 \quad \text{(Equation 4)}.$$

The ranges of X and Y that achieve LRV of 5 or higher satisfy the following equation 2 or 4 (based on the results of Experimental Example 24 (pH: 5, salt ionic strength: 50 mM) and Experimental Example 27 (pH: 6, salt ionic strength: 100 mM)):

$$0 \le Y \le 50X - 200 \quad \text{(Equation 2)}$$

$$Y = 0 \quad \text{(Equation 4)}.$$

In the case of LRV indicated by a value plus the mark ≥ (in the equation for calculation of LRV, $C_F$ (=the infectivity titer of the solution filtered through the small-pore size virus removal membrane) equal to or lower than the detection limit), the ranges of X and Y satisfy the following equation 3 or 4 (based on the results of Experimental Example 22 (pH: 5, salt ionic strength: 0 mM) and Experimental Example 29 (pH: 7, salt ionic strength: 100 mM)):

$$Y \le 50X - 250 \quad \text{(Equation 3)}$$

$$Y = 0 \quad \text{(Equation 4)}.$$

In general, the rate of virus removal by a small-pore size virus filtration membrane is rarely susceptible to the type of proteins prior to filtration. Thus, similar results were thought to be obtained even in the case of using protein solutions other than polyclonal antibody solutions. Also, a filtration pressure around 0.20 kgf/cm², for example, 0.30 kgf/cm² or lower, more specifically 0.10 kgf/cm² to 0.30 kgf/cm², further specifically 0.15 kgf/cm² to 0.25 kgf/cm², was thought to produce similar results.

Example 3

Filtration Through Small-pore Size Virus Removal Membrane Involving Post-wash Step Each protein solution (polyclonal antibody solution) having a combination of pH and salt ionic strength indicated as any of Experimental Examples 32 to 34 in Table 3 was prepared by the method described above in (i). Then, porcine parvovirus (PPV) was added at a concentration of 0.5 vol % to each solution, and the mixture was well stirred to obtain a virus-containing protein solution.

Each solution thus obtained was subjected to dead-end filtration through a small-pore size virus removal membrane (Planova (registered trademark) 20N) having a membrane area of 0.001 m² at a filtration pressure of 0.80 kgf/cm² (7.8×10 kPa) until the amount of the solution filtered reached 100 L/m² (the resulting filtrate is referred to as a virus filtration fraction). The filtration pressure was measured using a pressure gauge placed on the feed solution container side.

After reaching the predetermined amount of the solution filtered, the outlet line of the feed solution container was closed. Then, the pressure on the feed solution side (external) was first relieved to 0.0 kPa. Subsequently, the outlet line on the primary side (feed solution side via the membrane) of the filtration membrane was opened so that the internal pressure of the filtration membrane was also relieved to 0.0 kPa. Then, the filtration membrane was left for 3 hours.

Next, each washing solution (virus-free) having any of pHs and salt ionic strengths of Experimental Examples 32 to 34 shown in Table 3 was prepared in the same way as the method of (i) except that the polyclonal antibodies were not used. The feed solution container was switched to one containing the washing solution and pressurized to 0.80 kgf/cm² with the outlet line of the feed solution container closed. Then, the outlet line of the feed solution container was opened so that 5 L/m² of the washing solution was filtered at a pressure of 0.80 kgf/cm² (7.8×10 kPa) through the small-pore size virus removal membrane thus left (the resulting filtrate is referred to as a post-wash fraction).

The LRV of the virus filtration fraction was calculated by the method described above in (ii). The results are shown in Table 3. Also, the LRV' of only the post-wash fraction was calculated according to the following equation 7:

$$\text{LRV'} = \log_{10}(C_0/C_w) \quad \text{(Equation 7)}$$

wherein $C_0$ represents the virus concentration of the virus-containing protein solution prior to filtration, and $C_w$ represents the virus concentration of the filtrate of the washing solution after filtration of only the washing solution. The results are shown in Table 3.

In Experimental Example 34, the post-wash fraction had low LRV', although the virus filtration fraction had high LRV. This result demonstrated that viruses were leaked into the post-wash fraction obtained by the step involving filtration at a low filtration pressure (filtration pressure: 0.0 kPa). By contrast, in Experimental Examples 32 and 33, even the step involving such filtration at a low filtration pressure produced a high rate of virus removal.

TABLE 3

|  | pH | Salt ionic strength (mM) | LRV of virus filtration fraction | LRV' of post-wash fraction |
|---|---|---|---|---|
| Experimental Example 32 | 4.0 | 0 | ≥5.69 | ≥5.65 |
| Experimental Example 33 | 7.0 | 100 | ≥5.83 | ≥5.83 |
| Experimental Example 34 | 4.0 | 100 | ≥6.17 | 3.33 |

Example 4

Filtration Through Small-pore Size Virus Removal Membrane Involving Stop and Start Step Each protein solution (polyclonal antibody solution) having any of the pHs and salt ionic strengths of Experimental Examples 35 to 37 shown in Table 4 was prepared by the method described above in (i). Then, porcine parvovirus (PPV) was added at a concentration of 0.5 vol % to each solution, and the mixture was well stirred to obtain a virus-containing protein solution.

Each solution thus obtained was subjected to dead-end filtration through a small-pore size virus removal membrane (Planova (registered trademark) 20N) having a membrane area of 0.001 m² at a pressure of 0.80 kgf/cm² (7.8×10 kPa) until the amount of the solution filtered reached 100 L/m² (the resulting filtrate is referred to as a virus filtration fraction). The filtration pressure was measured using a pressure gauge placed on the feed solution container side.

After reaching the predetermined amount of the solution filtered, the outlet line of the feed solution container was closed. Then, the pressure on the feed solution side (external) was first relieved to 0.0 kPa. Subsequently, the outlet line on the primary side (feed solution side via the membrane) of the filtration membrane was opened so that the internal pressure of the filtration membrane was also relieved to 0.0 kPa. Then, the filtration membrane was left for 3 hours.

Next, the feed solution container was pressurized to 0.80 kgf/cm² with the outlet line of the feed solution container closed. Then, the outlet line of the feed solution container was opened so that 10 L/m² of the virus-containing protein solution was filtered again at a pressure of 0.80 kgf/cm² (7.8×10 kPa) through the small-pore size virus removal membrane thus left (the resulting filtrate is referred to as a stop & start fraction).

The LRV of the virus filtration fraction and the LRV of the stop & start fraction were calculated by the method described above in (ii). The results are shown in Table 4. In Experimental Example 37, the stop & start fraction had low LRV, although the virus filtration fraction had high LRV. This result demonstrated that viruses were leaked into the stop & start fraction obtained by the step involving filtration at a low filtration pressure (filtration pressure: 0.0 kPa). By contrast, in Experimental Examples 35 and 36, even the step involving such filtration at a low filtration pressure produced a high rate of virus removal.

TABLE 4

|  | pH | Salt ionic strength (mM) | LRV of virus filtration fraction | LRV of stop & start fraction |
|---|---|---|---|---|
| Experimental Example 35 | 4.0 | 0 | ≥5.12 | ≥5.12 |
| Experimental Example 36 | 7.0 | 100 | ≥5.74 | ≥5.74 |

TABLE 4-continued

| | pH | Salt ionic strength (mM) | LRV of virus filtration fraction | LRV of stop & start fraction |
|---|---|---|---|---|
| Experimental Example 37 | 4.0 | 100 | 6.42 | 3.59 |

As a result of these Examples 1 to 4, the ranges of the pH and salt ionic strength of the solution prior to filtration were found, which can satisfy a high rate of virus removal (PPV LRV: 4 or higher) even if the filtration of the virus-containing protein solution through the small-pore size virus removal membrane involves filtration at a low filtration pressure.

INDUSTRIAL APPLICABILITY

The present invention can provide a protein drug having a high rate of virus removal by the production of a virus-free protein drug using a small-pore size virus removal membrane, comprising a filtration step at a low filtration pressure. Thus, the present invention can provide a protein drug having a high rate of virus removal, for example, even by the filtration of a protein solution at a filtration pressure fixed to a low pressure, filtration involving a post-wash step, or filtration involving a stop and start step. Thus, the present invention has industrial applicability.

The invention claimed is:

1. A method for manufacturing a virus-free protein drug, comprising the following step (a):
  (a) filtering a virus containing protein solution through a small-pore size virus removal membrane to obtain a virus-free protein solution,
    comprising
    a low-pressure filtration step (q) of filtering a solution through the small-pore size virus removal membrane at a filtration pressure of 0.30 kgf/cm² or lower,
    wherein the solution prior to filtration in the low-pressure filtration step (q) has a pH (X) and a salt ionic strength (Y (mM)) that satisfy the following equations 1 and 5:

$0 \leq Y \leq 150X - 590$ (Equation 1)

$3.5 \leq X \leq 8.0$ (Equation 5)

or the following equations 4 and 5:

$Y = 0$ (Equation 4)

$3.5 \leq X \leq 8.0$, (Equation 5)

and
    a high-pressure filtration step (p) of filtering the virus-containing protein solution through the small-pore size virus removal membrane at a filtration pressure exceeding 0.30 kgf/cm², which is performed prior to the low-pressure filtration step (q),
    wherein the low-pressure filtration step (q) is a post-wash step or a stop and start step, and
    wherein pressurization is suspended during the filtration and then restarted in the stop and start step.

2. The method according to claim 1, wherein the solution prior to filtration in the step (q) is the virus-containing protein solution, and
  wherein 50% or more of the whole virus-containing protein solution to be filtered in the filtration step (a) is filtered in the low-pressure filtration step (q).

3. The method according to claim 1, wherein the filtration step (a) is a step of filtering the virus-containing protein solution through the small-pore size virus removal membrane at a filtration pressure of 0.30 kgf/cm² or lower to obtain the virus-free protein solution, wherein the solution prior to filtration in the filtration step (a) has a pH (X) and a salt ionic strength (Y (mM)) that satisfy the following equations 1 and 5:

$0 \leq Y \leq 150X - 590$ (Equation 1)

$3.5 \leq X \leq 8.0$ (Equation 5)

or the following equations 4 and 5:

$Y = 0$ (Equation 4)

$3.5 \leq X \leq 8.0$. (Equation 5)

4. The method according to claim 1, wherein the solution prior to filtration in the low-pressure filtration step (q) is a buffer solution for washing.

5. The method according to claim 1, wherein the filtration solution in the low-pressure filtration step (q) has a pH (X) and a salt ionic strength (Y (mM)) that satisfy the following equations 2 and 5:

$0 \leq Y \leq 50X - 200$ (Equation 2)

$3.5 \leq X \leq 8.0$ (Equation 5)

or the following equations 4 and 5:

$Y = 0$ (Equation 4)

$3.5 \leq X \leq 8.0$. (Equation 5)

6. The method according to claim 1, wherein the solution prior to filtration in the low-pressure filtration step (q) has a pH (X) and a salt ionic strength (Y (mM)) that satisfy the following equations 3 and 5:

$Y \leq 50 \leq X - 250$ (Equation 3)

$3.5 \leq X \leq 8.0$ (Equation 5)

or the following equations 4 and 5:

$Y = 0$ (Equation 4)

$3.5 \leq X \leq 8.0$. (Equation 5)

7. The method according to claim 1, wherein the low-pressure filtration step (q) is a step of filtering the solution through the small-pore size virus removal membrane at a filtration pressure of 0.20 kgf/cm² or lower to obtain the virus-free protein solution.

8. The method according to claim 1, wherein a log reduction value (LRV) calculated according to the following equation 6 is 4 or higher:

$LRV = \log_{10}(C_0/C_F)$ (Equation 6)

wherein $C_0$ represents the virus concentration of the virus-containing protein solution before the filtration step (a), and $C_F$ represents the virus concentration of the virus-free protein solution after the filtration.

9. The method according to claim 4, wherein a log reduction value (LRV) calculated according to the following equation 6 is 4 or higher:

$LRV = \log_{10}(C_0/C_F)$ (Equation 6)

wherein $C_0$ represents the virus concentration of the virus-containing protein solution before the filtration step (a), and $C_F$ represents the virus concentration of the virus-free protein solution after the filtration, and LRV' calculated according to the following equation 7 is 4 or higher:

$LRV = \log_{10}(C_0/C_w)$ (Equation 7)

wherein $C_0$ represents the virus concentration of the virus-containing protein solution before the filtration step (a), and $C_w$ represents the virus concentration of the filtrate of the buffer solution for washing after the filtration step (a).

10. The method according to claim 1, wherein the material of the small-pore size virus removal membrane is cellulose or a hydrophilized synthetic polymer.

11. The method according to claim 1, wherein the material of the small-pore size virus removal membrane is a hydrophilized synthetic polymer, and wherein the synthetic polymer is selected from the group consisting of polyvinylidene fluoride, polyether sulfone, polysulfone, and polyethylene.

12. The method according to claim 1, wherein the form of the small-pore size virus removal membrane is a flat membrane or a hollow fiber membrane.

13. The method according to claim 1, wherein the virus-containing protein solution has a protein concentration of 1 mg/mL to 100 mg/mL.

14. The method according to claim 1, wherein the virus-containing protein solution comprises one or more protein(s) selected from the group consisting of monoclonal antibodies, recombinant blood coagulation factor, interferon, hormones, enzymes, immunoglobulin, albumin, blood coagulation factor VIII, blood coagulation factor IX, fibrinogen, and antithrombin III.

15. The method according to claim 1, wherein the virus-containing protein solution comprises an antibody as the protein.

16. The method according to claim 1, wherein the virus-containing protein solution comprises blood coagulation factor VIII or fibrinogen as the protein.

17. The method according to claim 1, wherein the virus-containing protein solution comprises one or more virus(es) selected from the group consisting of human parvovirus B19 (B19), minute virus of mice (MVM), porcine parvovirus (PPV), bovine parvovirus (BPV), canine parvovirus (CPV), poliovirus (Polio), circovirus, hepatitis A virus (HAV), and hepatitis E virus (HEV).

18. The method according to claim 1, wherein the virus-containing protein solution comprises a virus of 32 nm or smaller in diameter having no envelope.

19. The method according to claim 1, wherein the virus-containing protein solution comprises one or more component(s) selected from the group consisting of an inorganic salt, a buffer solution component, a surfactant, and a saccharide.

20. A method for manufacturing a virus-free protein drug, comprising the following step (a):

(a) filtering a virus containing protein solution through a small-pore size virus removal membrane to obtain a virus-free protein solution,
comprising
a low-pressure filtration step (q) of filtering a solution through the small-pore size virus removal membrane at a filtration pressure of 0.30 kgf/cm² or lower, and
comprising, prior to the low-pressure filtration step (q), a step of adjusting the solution prior to filtration so that the solution prior to filtration in the step (q) has a pH (X) and a salt ionic strength (Y (mM)) that satisfy the following equations 1 and 5:

$0 \leq Y \leq 150X - 590$ (Equation 1)

$3.5 \leq X \leq 8.0$ (Equation 5)

or the following equations 4 and 5:

$Y = 0$ (Equation 4)

$3.5 \leq X \leq 8.0$, (Equation 5)

and
further comprising, prior to the low-pressure filtration step (q), a high-pressure filtration step (p) of filtering the virus-containing protein solution through the small-pore size virus removal membrane at a filtration pressure exceeding 0.30 kgf/cm²,
wherein the low-pressure filtration step (q) is a post-wash step or a stop and start step, and
wherein pressurization is suspended during the filtration and then restarted in the stop and start step.

21. The method according to claim 1, wherein a log reduction value (LRV) calculated according to the following equation 6 is 4 or higher:

$LRV = \log_{10}(C_0/C_F)$ (Equation 6)

wherein $C_0$ represents the virus concentration of the virus-containing protein solution before the filtration step (a), and $C_F$ represents the virus concentration of the virus-free protein solution after the filtration, and LRV' calculated according to the following equation 7 is 4 or higher:

$LRV = \log_{10}(C_0/C_w)$ (Equation 7)

wherein $C_0$ represents the virus concentration of the virus-containing protein solution before the filtration step (a), and $C_w$ represents the virus concentration of the filtrate of the buffer solution for washing after the filtration step (a).

* * * * *